United States Patent
Jackson

[19]

[11] Patent Number: 5,897,530
[45] Date of Patent: Apr. 27, 1999

[54] ENCLOSED AMBULATORY PUMP

[75] Inventor: Roger W. Jackson, Mission Viejo, Calif.

[73] Assignee: Baxter International Inc., Deerfield, Ill.

[21] Appl. No.: 08/997,787

[22] Filed: Dec. 24, 1997

[51] Int. Cl.$^6$ .................................................. A61M 37/00
[52] U.S. Cl. ............................................................ 604/132
[58] Field of Search .................................. 604/132, 131, 604/DIG. 12

[56] References Cited

U.S. PATENT DOCUMENTS

| | | |
|---|---|---|
| 3,760,806 | 9/1973 | Leeper . |
| 4,201,207 | 5/1980 | Buckles et al. . |
| 4,386,929 | 6/1983 | Peery et al. . |
| 4,419,096 | 12/1983 | Leeper et al. . |
| 4,741,733 | 5/1988 | Winchell et al. . |
| 4,904,239 | 2/1990 | Winchell et al. . |
| 5,061,243 | 10/1991 | Winchell et al. . |
| 5,083,678 | 1/1992 | Waring . |
| 5,137,175 | 8/1992 | Kowalski et al. . |
| 5,178,610 | 1/1993 | Tsujikawa et al. . |
| 5,298,025 | 3/1994 | Hessel et al. ..................... 128/DIG. 12 |

FOREIGN PATENT DOCUMENTS

| | | |
|---|---|---|
| 0032792 | 7/1981 | European Pat. Off. . |
| 0172586 | 2/1986 | European Pat. Off. . |
| 0211850 | 3/1987 | European Pat. Off. . |
| 0290586 | 11/1988 | European Pat. Off. . |
| 0295504 | 12/1988 | European Pat. Off. . |
| 0473781 | 3/1992 | European Pat. Off. . |
| 0464761 | 9/1994 | European Pat. Off. . |
| 0426319 | 5/1995 | European Pat. Off. . |
| 0665028 | 8/1995 | European Pat. Off. . |
| 2672803 | 9/1992 | France . |
| 1135360 | 5/1989 | Japan . |
| 8196628 | 6/1996 | Japan . |
| 2115494 | 9/1983 | United Kingdom . |
| 9112835 | 4/1991 | WIPO . |
| 9206721 | 4/1992 | WIPO . |
| 9310831 | 6/1993 | WIPO . |
| 9320884 | 10/1993 | WIPO . |
| 9425100 | 11/1994 | WIPO . |
| 9514503 | 6/1995 | WIPO . |
| 9639210 | 12/1996 | WIPO . |

*Primary Examiner*—Jeffrey A. Smith
*Attorney, Agent, or Firm*—Jeffrey C. Nichols; Mark J. Buonaiuto; Francis C. Kowalik

[57] ABSTRACT

An ambulatory pump (10) for dispensing a liquid under pressure at a predetermined flow rate includes a housing (12) having first and second end caps (14, 16) positioned on the housing (12) and enclosing the housing (12). Each end cap (14,16) has a port (18,20) formed therein. A pressurizable bladder (22) is carried by the housing (12) for receiving and dispensing the liquid. The bladder (22) is expandable between an unexpanded condition and an expanded condition. The bladder (22) has a free end (30) defining an opening in flow communication with the second end cap port (20) and a fixed end defining an opening in flow communication with the first end cap port (18). A section of flexible tubing (40) is carried by the housing (12) and extends between and is in flow communication with the bladder free end (30) opening and the second end cap port (20). The pump (10) includes a connecting member (32) positioned between the flexible tubing (40) and the bladder (22) that is configured to provide indication of the volume of the pump (10). The connecting member (32) moves longitudinally within the housing (12) to indicate the volume of liquid in the pump (10) as the bladder (22) moves between the expanded and unexpanded conditions. The pump (10) includes an inlet port (20) at the second end cap (16) and a tubing set (50) extending from the first end cap port (18) to dispense the liquid to a patient.

8 Claims, 1 Drawing Sheet

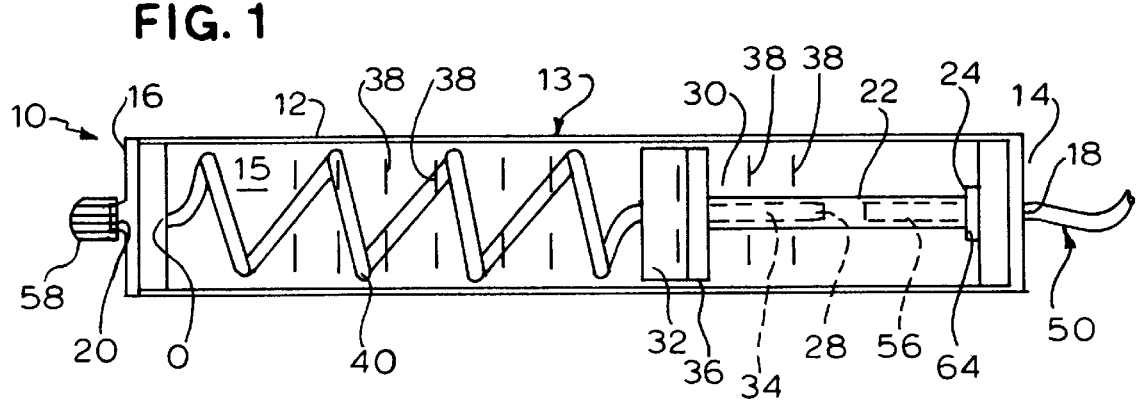
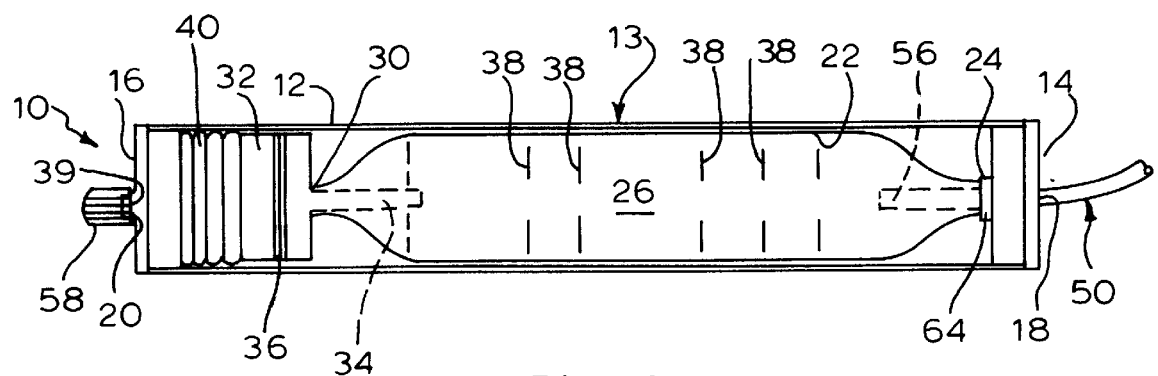
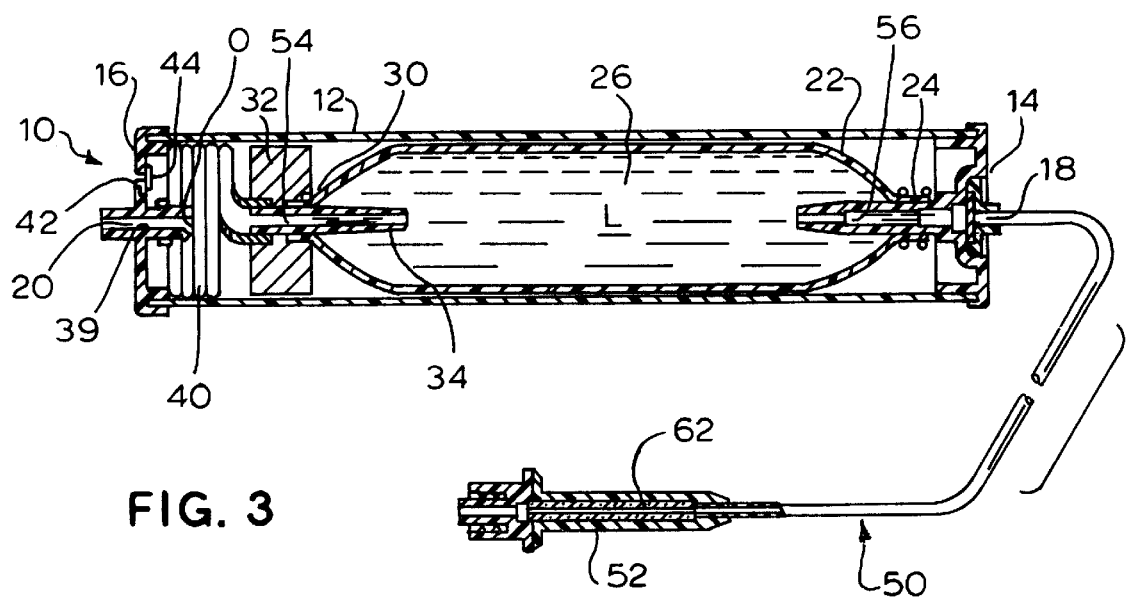

ENCLOSED AMBULATORY PUMP

FIELD OF THE INVENTION

This invention pertains to an enclosed ambulatory pump. More particularly, the invention pertains to an enclosed ambulatory pump having an expandable or pressurizable bladder for storing and dispensing liquid to a patient.

BACKGROUND OF THE INVENTION

Ambulatory pumps or infusors are well known in the art. Such devices are used for delivering a predetermined quantity of a drug or other medicament to a patient in a preselected time period at a substantially constant fluid flow rate. One known pump includes a tubular, elastomeric, pressurized bladder that contains the liquid to be infused. The bladder is pressurized by the liquid stored therein. The pump includes a housing, a plug fixed in one end of the housing and an aperture that extends through the plug. One end of the bladder is sealingly attached to the plug, with the lumen of the bladder communicating with the aperture of the plug. The pump includes a conduit, such as a tube set connected to the plug aperture that defines a dispensing passageway for transporting the liquid from the bladder to the infusion site for the patient.

A flow regulator is disposed within the dispensing passageway for permitting the liquid to flow from the bladder through the dispensing passageway, to, for example, a patient, at a predetermined rate. The flow regulator or restrictor includes a capillary element.

The pump includes a "floating" or movable cap or indicator affixed to a free end of the bladder. The indicating member floats or moves longitudinally within the housing dependent upon the fill of the bladder. The indicating member includes a passageway, a one-way valve positioned at about the passageway and inlet or fill port through which the bladder is filled. The port and passage are in flow communication with the bladder.

In order to fill the bladder it is necessary to grasp the indicator by pinching or inwardly flexing the sides of the housing and inserting a fill device such as a syringe into the housing. The syringe is then connected to the fill port and the liquid is transferred from the syringe into the bladder. Typically, the syringe to fill port connection includes a threaded portion which forms a tight seal between the syringe and the fill port. As the bladder is filled, the indicating member is allowed to move to accommodate the expanding bladder.

While this known pump works well for its intended purpose, there are a number of drawbacks. First, the exterior of the bladder is essentially open to atmosphere by virtue of the floating characteristics of the indicator. Thus, in the event that the bladder ruptures, the liquid from the bladder will escape into the housing. An end cap positioned on the housing retains the liquid in the housing in the event of bladder rupture. However, the end cap is typically packaged separately from the housing, and, if improperly positioned on the housing, can result in leakage from the housing if the bladder ruptures.

In addition, the "floating" nature of the indicator can at times make it difficult to fill the infusion device because the indicator must be grasped through the housing wall. Because the indicator "floats" the bladder can be twisted as the syringe is threaded onto the inlet port. As will be apparent, twisting the elastomeric bladder can weaken the elastomeric material, thus increasing the opportunity for rupture. In addition, problems have been encountered that, it is believed, are a result of turbulence in the liquid during filling of the pump. Specifically, as the liquid "breaks" through the one-way valve, the flow resistance causes turbulence in the liquid, which, in turn, results in the entrainment of air in the liquid. The entrained air forms microbubbles in the liquid. It has been observed that these microbubbles can accumulate at the capillary in the flow restrictor. Those skilled in the art will recognize that the microbubble accumulation can result in blockage of fluid flow through the capillary.

Accordingly, there continues to be a need for an ambulatory pump that fully encloses the infusion bladder, which facilitates filling of the storage bladder and minimizes the opportunity to rupture the bladder. Such a device will be readily used with standard medical apparatus hardware, and will reduce the priming problems and flow restrictions encountered in known pump devices.

SUMMARY OF THE INVENTION

An ambulatory pump for dispensing a liquid under pressure at a predetermined flow rate comprises a housing having first and second fixed end caps positioned on the housing and enclosing the housing. Each of the end caps has a port formed therein. A pressurizable bladder that defines an interior storage volume is carried by the housing for receiving and dispensing the liquid.

The bladder is expandable between an unexpanded condition and an expanded condition. The bladder has a free end defining an opening in flow communication with the second end cap port and a fixed end defining an opening in flow communication with the first end cap port.

A section of flexible tubing is carried by the housing and extends between and is in flow communication with the bladder free end opening and the second end cap port.

In a preferred embodiment the pump includes a connecting member positioned between the flexible tubing and the bladder. The connecting member is longitudinally movable within the housing as the bladder moves between the expanded condition and the unexpanded condition. In a most preferred embodiment, the housing is formed of a transparent or translucent material and includes indicia thereon. Most preferably, the connecting member is an indicator and includes indicia that, in cooperation with the housing indicia, indicates the volume of liquid in the pump.

The pump includes an inlet or fill port formed in the second end cap port that is in flow communication with the flexible tubing and the bladder. In a preferred embodiment, the fill port is formed with a female Luer-type connection and the pump includes a protective cap formed with a male Luer-type fitting to matingly engage the fill port.

The pump includes a tubing set extending from the first end cap port, in flow communication with the bladder. Preferably, the tubing set includes a flow restrictor therein.

The pump includes at least one valve positioned therein to permit flow of liquid into the bladder, and to prevent reverse flow therefrom. Preferably, the valve is positioned on the indicating member extending inwardly of the expandable bladder. In a current embodiment, the valve is configured as a duck-bill valve.

In order to accommodate the expanding volume of the bladder, the pump includes at least one vent formed in one of the end caps. The vent is configured to permit egress and ingress of air to maintain the interior of the housing at about atmospheric pressure. In a most preferred embodiment, the vent opening is covered with a hydrophobic material that permits the passage of air or gas therethrough and prevents the passage of liquid therethrough.

Other features and advantages of the present invention will be apparent from the following detailed description, the accompanying drawings, and the appended claims.

BRIEF DESCRIPTION OF THE FIGURES.

FIG. 1 is a side view of an enclosed ambulatory pump embodying the principles of the present invention, the pump being shown with the bladder in the unexpanded condition;

FIG. 2 is an illustration of the ambulatory pump of FIG. 1, with the bladder in the expanded condition; and FIG. 3 is a cross-sectional view of the pump of FIG. 2, the pump being shown with a tube set and flow restrictor connected thereto.

DETAILED DESCRIPTION OF THE PROFFERED EMBEDMENTS

While the present invention is susceptible of embodiment in various forms, there is shown in the drawings and will hereinafter be described a presently preferred embodiment with the understanding that the present disclosure is intended to be considered an exemplification of the invention and is not intended to limit the invention to the specific embodiment illustrated.

Referring now to the figures, and in particular to FIG. 1 there is shown an ambulatory pump 10 embodying the principles of the present invention. The pump 10 includes a main body portion or housing 12 and first and second end caps 14, 16, respectively, enclosing the housing 12. The housing 12, first end cap 14 and second end cap 16 form a shell 13 which defines an interior chamber 15. Preferably the housing 12 is formed of a transparent or translucent plastic material. Each of the first and second end caps 14, 16 includes a port 18, 20, respectively. An expandable bladder or reservoir 22 is positioned within the chamber 15, and is fixedly connected to one of the end caps 18 at a fixed end 24. The expandable bladder 22 includes an interior storage volume 26 that, in the unexpanded state or condition (as illustrated in FIG. 1), essentially defines a lumen as indicated at 28. The lumen 28 or interior storage volume 26 is in flow communication with the port 18 on the end cap 14 to which the bladder 22 is fixedly connected. For purposes of the present description, this will be referred to as the first end cap 14.

Conversely, the opposing cap will be referred to as the second end cap 16.

The free end 30 of the bladder 22 is mounted to a "floating" or movable element 32, such as the illustrated connecting or indicating member or indicator. The "floating" element 32 includes a port 34 to which the expandable bladder 22 is connected and with which the lumen 28 or storage volume 26 is in flow communication. As illustrated, the element 32 can include indicia 36 to, in cooperation with indicia 38 on the housing 12, permit determining the volume of liquid L in the pump 10.

At least a portion or section of flexible tubing 40 extends between the indicating member 32 and an opening O formed by the tubing 40 for filling the bladder 22. Preferably, the opening O is in flow communication with an inlet 39 formed by the second end cap port 20. Most preferably, the flexible tubing 40 is in flow communication with both the port 34 through the indicating member 32 and the port 20 in the second end cap 16. In this arrangement, an essentially isolated fluid storage and transport circuit is established from the second end cap 16 through the port 20 into the flexible tubing 40, through the indicator 32 and bladder 22, and out of the port 18 in the first end cap 14. The tube 40 has a relatively small inside diameter to minimize the amount of residual fluid that may be in the pump system after infusion. The small diameter tube also reduces or minimizes the time necessary for priming the pump 10. However, as will be discussed in more detail herein, the minimal amount of air (about 0.50 ml) in the tubing 40 enhances operation of the pump 10.

As will be apparent from FIGS. 1 and 2, the flexible tubing 40 permits expansion and contraction of the bladder 22. In a preferred embodiment, the tubing 40 coils onto itself (as seen in FIG. 2) as the bladder 22 expands. This results in a minimum amount of space occupied by the tubing 40 when the bladder 22 is fully expanded. Additionally, coiling of the tubing 40 reduces or eliminates the opportunity for the tubing to "pinch" as it moves within the housing 12 as the bladder 22 expands.

In a preferred embodiment, the pump 10 includes at least one vent opening 42, the function of which will be described in more detail herein. Most preferably, the vent opening 42 is formed in one of the end caps 14, 16. In a present embodiment, the second end cap 16 includes an opening 42, which is covered with a hydrophobic material 44. The hydrophobic material 44 permits the passage of air therethrough, and prevents the passage of liquid.

In a present embodiment, a tube set 50 is connected to the pump 10, which tube set 50 is configured to provide fluid, directly or indirectly from the bladder 22 to a patient. An exemplary arrangement illustrated in FIG. 3, including a flow restrictor 52 positioned within the tube set 50, is disclosed in U.S. Pat. No. 4,904,239 to Winchell et al., which patent is commonly assigned herewith, and which is incorporated herein by reference. The patient delivery tube set 50 can be connected to the end cap 14 of the pump 10. Preferably the tube set 50 is connected to (e.g., formed as a part of) the pump 10 assembly.

For purposes of the present discussion, the second end cap port 20 will be referred to as the inlet or fill port 20 and the first cap port 18 will be referred to as the outlet port. The pump 10 includes at least one valve 54 that is configured to permit fluid L to flow into the bladder 22 from the inlet port 20 to fill the bladder 22. In a present configuration, a "duck bill" valve 54 is formed as part of, or mounted to, the indicating member 32, extending into the bladder 22. The duck bill valve 54 permits fluid L input to the bladder 22 from the inlet port 20 and prevents reverse flow out of the bladder 22 through the inlet port 20.

The pump 10 further includes an outlet nozzle 56 that extends inwardly from the first end cap 14 at the port 18, into the bladder 22. In this configuration, the bladder 22 can be sealingly mounted to the port 34 and to the nozzle 56 to isolate the fluid path, and to prevent leakage from around the bladder 22 connections into the housing 12. The outlet nozzle 56 can be configured to filter flow from the bladder 22. Alternately, and preferably, the outlet nozzle 56 is configured to provide a free flow of fluid that can be regulated by a downstream restrictor device 52, such as that disclosed in the above-noted patent to Winchell et al.

The inlet port 20 can include a mounting and connection configuration, such as a Luer lock type of arrangement so that the pump 10 can be filled using standard, known medical devices.

Preferably, the inlet port 20 can be fitted with a protective cap 58 to protect the port 20 connection, to assure structural integrity of the pump 10, and to reduce the opportunity for contamination of the pump 10 and liquid L. In a current embodiment, the inlet port 20 is formed having a female Luer lock connection and the protective cap 58 is formed with a male Luer lock connection for matingly engaging the inlet port 20.

Advantageously the present ambulatory pump 10 eliminates the need to inwardly flex or pinch the housing in order to grasp the indicator element to fill the bladder. Rather, because the inlet port 20 is positioned on a rigid cap 16 that is connected to the elastomeric bladder 22 by a section of flexible tubing 40, the cap 16 or housing 12 at about the cap 16 can be grasped, and a liquid supply source, such as a syringe, can be connected to the inlet port 20 to fill the bladder 22. Thus, when connecting the syringe or other supply source to the pump 10, any twisting or torquing motion, such as is necessary when using a Luer-type connector, is transferred only to the rigid port 20, rather than transferred to the bladder 22.

Referring now to FIG. 2, as the bladder 22 is filled, it expands. The force from the expanding bladder 22 on the indicator 32 moves the indicator 32 toward the inlet port 20. As the indicator 32 moves toward the inlet port 20, the flexible tubing 40 will coil to accommodate the expanding bladder 22. When the desired amount of fluid is input to the bladder 22, the supply source can be disconnected and the protective cap 58 replaced on the port 20. Replacing the cap 58 at this time reduces the opportunity to damage the port 20 or to contaminate the fluid L in the device 10.

It will be recognized by those skilled in the art that as the bladder 22 expands, the air that would otherwise be in the housing 12 must be exhausted from the device 10 to maintain the chamber 15 within the housing 12 at about atmospheric pressure. Although the vent opening 42 in the end cap 16 is sufficiently sized to permit the ingress or egress of air to maintain the housing 12 at about atmospheric pressure, it is sufficiently small such that rupture of the bladder 20 and consequent loss of liquid L therefrom will be contained within the housing 12. As provided above, in a preferred embodiment, the vent opening 42 is covered with a hydrophobic material 44. Such a material, which will be recognized by those skilled in the art, permits air or another gas to substantially pass through the material 44 to maintain the space 45 within the housing 12 substantially at atmospheric pressure, while it prevents passage of liquids, such as water in the event that the bladder 22 ruptures.

It is anticipated that the various components of the present ambulatory pump 10 will be formed of known, presently used, medically acceptable materials. Those skilled in the art will recognize that these materials can be bonded to one another using various, known, medically acceptable techniques. For example, the end caps 14, 16 can be bonded to the housing 12 by solvent bonding. The bladder 22 can be mounted to the port 34 located on the indicator 32 and to the outlet nozzle 56 by mechanical attachment, such as the illustrated band 64 or the like.

Advantageously, the present ambulatory pump 10 addresses the problems that have been encountered with known pump devices. As provided above, there is a small amount of air in the flexible tubing 40 between the inlet port 20 and the bladder 22, prior to filling the pump 10. It has been found that when this "slug" of air is forced through the duck-bill valve 54, prior to the introduction of liquid through the valve 54, rather than the immediate introduction of liquid as is the case in known pumps, there is substantially less entrainment of air in the liquid that is introduced into the bladder 22. As will be apparent to those skilled in the art, this reduced entrainment of air results in a substantial reduction or elimination of microbubbles that would otherwise be formed in the liquid. While not wanting to be limited to the theory provided, it is believed that this reduction or elimination of microbubbles reduces the opportunity for accumulation of such bubbles at the regulator capillary 62. This, in turn, reduces the opportunity for problems in priming the pump 10 or clogging at the restrictor 52.

From the foregoing it will be observed that numerous modifications and variations can be effectuated without departing from the true spirit and scope of the novel concepts of the present invention. It is to be understood that no limitation with respect to the specific embodiment illustrated is intended or should be inferred. The disclosure is intended to cover by the appended claims all such modifications as fall within the scope of the claims.

What is claimed is:

1. An ambulatory pump for dispensing a liquid under pressure at a predetermined flow rate comprising:

a housing;

first and second fixed end caps positioned on the housing and enclosing the housing, each of the end caps having a port formed therein;

a pressurizable bladder defining an interior storage volume, the bladder being carried by the housing for receiving and dispensing the liquid, the bladder being expandable between an unexpanded condition and an expanded condition, the bladder having a free end defining an opening in flow communication with the second end cap port and a fixed end defining an opening in flow communication with the first end cap port; and flexible tubing carried by the housing, the flexible tubing extending between and in flow communication with the bladder free end opening and an opening for filling the bladder with liquid.

2. The ambulatory pump in accordance with claim 1 wherein the opening in the flexible tubing for filling the bladder with liquid is connected to and in flow communication with a port on the second end cap.

3. The ambulatory pump in accordance with claim 1 including a connecting member positioned between the flexible tubing and the bladder, the connecting member being longitudinally movable within the housing as the bladder moves between the expanded condition and the unexpanded condition.

4. The ambulatory pump in accordance with claim 3 wherein the housing is formed of a transparent material.

5. The ambulatory pump in accordance with claim 4 wherein the connecting member is an indicator and includes indicia thereon, and wherein the housing includes indicia which, in cooperation with the indicia on the indicator indicates a determinable volume of fluid in the pump.

6. The ambulatory pump in accordance with claim 1 wherein one of the end caps includes a vent opening.

7. The ambulatory pump in accordance with claim 6 wherein the vent opening includes a covering formed of a hydrophobic material.

8. The ambulatory pump in accordance with claim 1 including a tubing set connected to the pump at the first end cap port, the tubing set including a flow restrictor.

* * * * *